(12) United States Patent
Wu et al.

(10) Patent No.: US 10,610,168 B2
(45) Date of Patent: Apr. 7, 2020

(54) NURSING CALL SYSTEM AND MEASURING METHOD THEREOF

(71) Applicant: MELTEN CONNECTED HEALTHCARE INC., Grand Cayman (KY)

(72) Inventors: Fang-Chi Wu, New Taipei (TW); Yen-Ming Huang, New Taipei (TW); Yun-Tse Hsiao, New Taipei (TW); Chia-Chien Chang, New Taipei (TW)

(73) Assignee: MELTEN CONNECTED HEALTHCARE INC., Grand Cayman (KY)

( * ) Notice: Subject to any disclaimer, the term of this patent is extended or adjusted under 35 U.S.C. 154(b) by 0 days.

(21) Appl. No.: 16/196,348

(22) Filed: Nov. 20, 2018

(65) Prior Publication Data
US 2019/0246994 A1 Aug. 15, 2019

Related U.S. Application Data

(60) Provisional application No. 62/628,404, filed on Feb. 9, 2018.

(51) Int. Cl.
*G08B 5/22* (2006.01)
*A61B 5/00* (2006.01)
*G08B 21/04* (2006.01)
*A61B 5/024* (2006.01)
*A61B 5/044* (2006.01)

(52) U.S. Cl.
CPC .............. *A61B 5/746* (2013.01); *A61B 5/002* (2013.01); *A61B 5/02416* (2013.01); *A61B 5/044* (2013.01); *G08B 21/0461* (2013.01); *G08B 21/0492* (2013.01)

(58) Field of Classification Search
CPC ............................ G08B 21/0492; A61B 5/746
USPC ....................................................... 340/286.7
See application file for complete search history.

(56) References Cited

U.S. PATENT DOCUMENTS

| 9,788,735 B2 * | 10/2017 | Al-Ali | ................. A61B 5/02438 |
| 2015/0302539 A1 * | 10/2015 | Mazar | ................. G08B 21/0211 705/3 |
| 2017/0042488 A1 * | 2/2017 | Muhsin | .................. A61B 5/742 |

* cited by examiner

*Primary Examiner* — Tai T Nguyen
(74) *Attorney, Agent, or Firm* — Muncy, Geissler, Olds & Lowe, P.C.

(57) ABSTRACT

A nursing call system includes an emergency call device, a display screen and an extension accessory. The extension accessory includes a connecting wire, a connecting end and a holding device. The connecting end is connected to one end of the connecting wire and is used to connect a connection member of the emergency call device. The holding device is connected to the other end of the connecting wire and includes a first physiological sensor and a second physiological sensor. The first physiological sensor includes a sensing component and is disposed to measure a first physiological information. The second physiological sensor is disposed to measure a second physiological information and includes a first sensing component and a second sensing component. The second sensing component and both of the first sensing component and the sensing component are respectively disposed at two different regions of the holding device.

10 Claims, 6 Drawing Sheets

NURSING CALL SYSTEM AND MEASURING METHOD THEREOF

CROSS-REFERENCE TO RELATED APPLICATIONS

The present application claims the benefit of U.S. provisional application Ser. No. 62/628,404 filed on Feb. 9, 2018 which is incorporated herein by reference.

TECHNICAL FIELD

The present invention relates to a nursing call system and a measuring method thereof, and in particular to a nursing call system and a measuring method thereof capable of measuring physiological information.

BACKGROUND

In the conventional medical system, an emergency call system is set up in the ward for a patient to notify the nursing staff in an emergency, so that the nursing staff can be present to assist.

In addition, in the conventional medical system, the nursing staff measures the physiological information of the patient through a physiological measuring device for subsequent medical use. The measured physiological information needs to be manually input into a hospital system by the nursing staff. In this way, there are a number of disadvantages. For example, manual input may result in input errors so as to affect subsequent medical judgments, or for quite busy nursing staff, regularly measuring the patient's physiological information and manual input increase the workload of the nursing staff.

In view of this, the disclosure provides a nursing call system and a measuring method thereof, which effectively integrate the above-mentioned emergency call system and physiological measuring device to improve the problems existing in the prior art.

SUMMARY

The invention discloses a nursing call system including an emergency call device, a display screen and an extension accessory. The emergency call device includes a connection member and is disposed adjacent to a bed to transmit an emergency call signal to a nursing station. The extension accessory includes a connecting wire, a connecting end and a holding device. The connecting end is connected to one end of the connecting wire to connect the connection member of the emergency call device to enable electrical connection between the extension accessory and the emergency call device.

The holding device is connected to the other end of the connecting wire and includes a first physiological sensor and a second physiological sensor. The first physiological sensor includes a sensing component and is disposed to measure a first physiological information. The second physiological sensor is disposed to measure a second physiological information and includes a first sensing component and a second sensing component. The first sensing component and the sensing component of the first physiological sensor are disposed adjacent to each other and disposed at a first region of the holding device. The second sensing component is disposed at a second region of the holding device. The first region is separated from the second region.

The measured first physiological information and the second physiological information are displayed on the display screen when a finger of a first hand of a patient on the bed contacts the sensing component of the first physiological sensor and the first sensing component, and a limb of the patient contacts the second sensing component.

In an embodiment of the invention, the first physiological sensor is a photo-plethysmographic sensor, and the second physiological sensor is an electrocardiographic sensor.

In an embodiment of the invention, the holding device further includes a carrier and a hole. The carrier forms the first region and is fixed in the hole. An alignment direction of the sensing component of the first physiological sensor and the first sensing component of the second physiological sensor located on the carrier is oriented toward an opening of the hole. The second region is a portion of an outer surface of the holding device. The carrier has a recess to carry the sensing component of the first physiological sensor.

In an embodiment of the invention, the holding device further includes a hollow elastic member disposed in the hole. An expanding direction of the hollow elastic member is toward the sensing component of the first physiological sensor.

In an embodiment of the invention, the holding device further includes an emergency call button disposed at an upper end of the holding device to trigger the emergency call signal.

In an embodiment, the invention discloses a nursing call system including an emergency call device, a display screen and an extension accessory. The emergency call device includes a connection member and is disposed adjacent to a bed to transmit an emergency call signal to a nursing station. The extension accessory includes a connecting wire, a connecting end and a holding device. The connecting end is connected to one end of the connecting wire to connect the connection member of the emergency call device to enable electrical connection between the extension accessory and the emergency call device. The holding device is disposed at the other end of the connecting wire and includes an emergency call button, a hole, and a physiological sensor assembly. The emergency call button is disposed at an upper end of the holding device to trigger the emergency call signal. The physiological sensor assembly is disposed to measure at least one physiological information displayed on the display screen. At least one sensing component of the physiological sensor assembly is disposed in the hole to be contacted by a finger of a first hand of a patient on the bed to obtain the at least one physiological information.

In an embodiment of the invention, the at least one sensing component includes a first sensing component, and the physiological sensor assembly further includes a second sensing component. The first sensing component is disposed in the hole, and the second sensing component is disposed on an outer surface of the holding device. The hole is inclined toward the upper end of the holding device, and an angle between the hole and a center line of the holding device in the up and down direction is between 105 degrees and 170 degrees.

The invention further discloses a measuring method of a nursing call system, including the following steps:

To determine whether a connecting end of an extension accessory is connected to a connection member of an emergency call device. The nursing call system includes the emergency call device, the extension accessory and a display screen. The emergency call device is disposed adjacent to a bed to transmit an emergency call signal to a nursing station.

The emergency call device includes the connecting member, and the extension accessory includes a connecting wire, the connecting end and a holding device. The connecting end is disposed at one end of the connecting wire and disposed to connect the connecting member of the emergency call device to enable electrical connection between the extension accessory and the emergency call device. The holding device is disposed at the other end of the connecting wire.

To display a measuring button on the display screen.

To pass a finger of a first hand of a patient on the bed into a hole and contact at least one sensing component of a physiological sensor assembly. The holding device includes the hole and the physiological sensor assembly disposed to measure at least one physiological information. The at least one sensing component of the physiological sensor assembly is disposed in the hole.

To press the measuring button to measure the at least one physiological information and present the at least one physiological information on the display screen.

In an embodiment, the measuring method further includes a step of verifying a caregiver identifier. The at least one physiological information is measured when the caregiver identifier is verified by the nursing call system as a caregiver.

In an embodiment, the measuring method further includes a step of verifying a caregiver identifier and uploading the at least one physiological information. The at least one physiological information is uploaded when the caregiver identifier is verified by the nursing call system as a caregiver.

The invention enables the physiological information to be transmitted directly and in real time to the medical information system through the nursing call system by integrating the physiological sensor assembly into the nursing call system. In this way, the workload of manual input by a caregiver can be reduced, the possible errors due to manual input can be avoided, and the real-time updating of the medical information system is helpful for real-time medical use.

In addition, the invention can reduce the influence of external light on the physiological sensor through the design of the hole and/or the design of a recess of a carrier plate, so that the physiological sensing result is more accurate.

Various other objects, advantages and features of the present invention will become readily apparent from the ensuing detailed description accompanying drawings, and the novel features will be particularly pointed out in the appended claims.

BRIEF DESCRIPTION OF DRAWINGS

The following detailed descriptions, given by way of example, and not intended to limit the present invention solely thereto, will be best be understood in conjunction with the accompanying figures.

DETAILED DESCRIPTION OF THE EMBODIMENTS

Figure 1A:
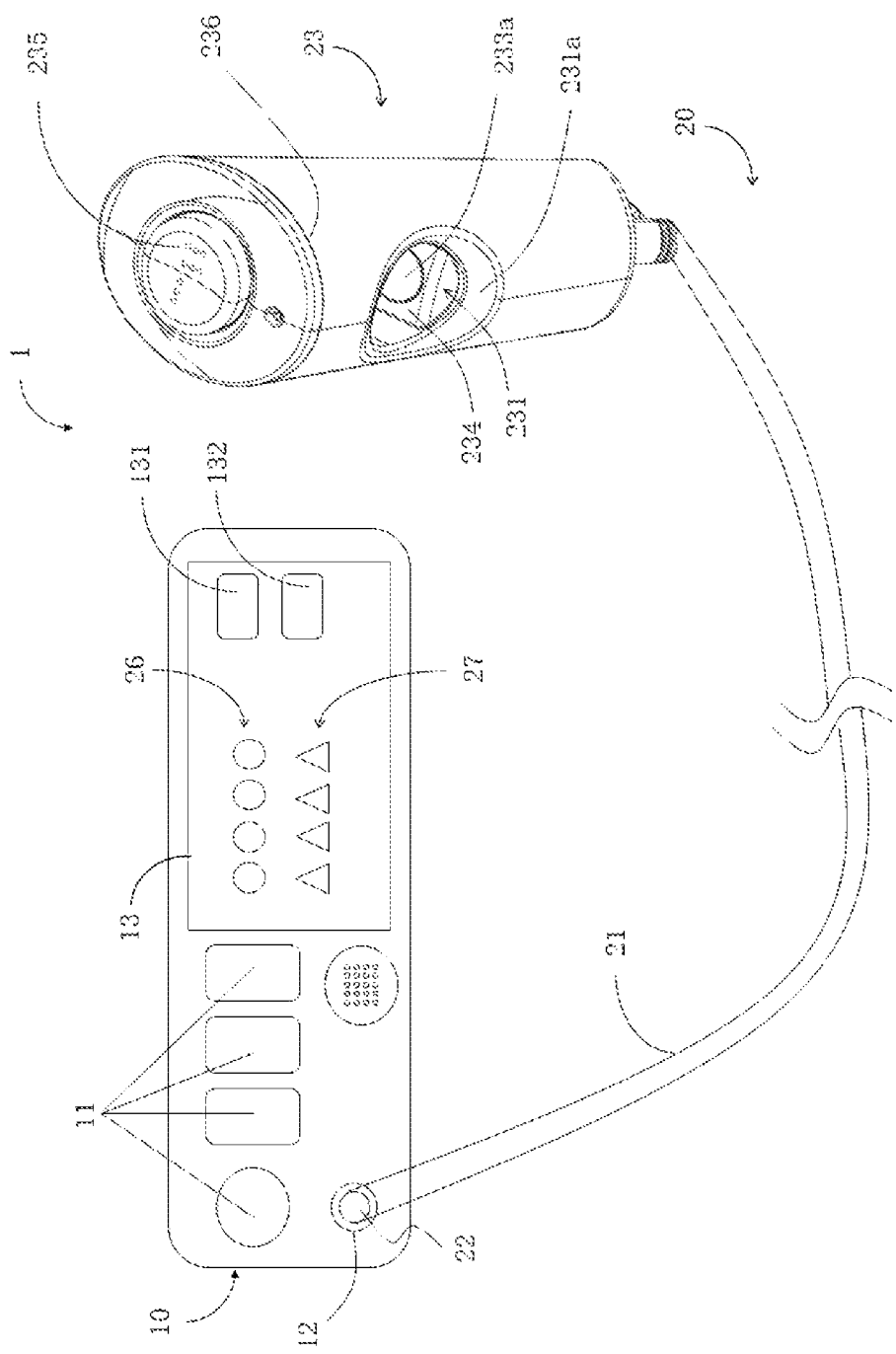
FIG. 1 A is a schematic diagram of a nursing call system according to an embodiment of the present invention.
FIGS. 1B-1C are schematic views of different perspectives of the holding device of the nursing call system of FIG. 1A.
Figure 1B:
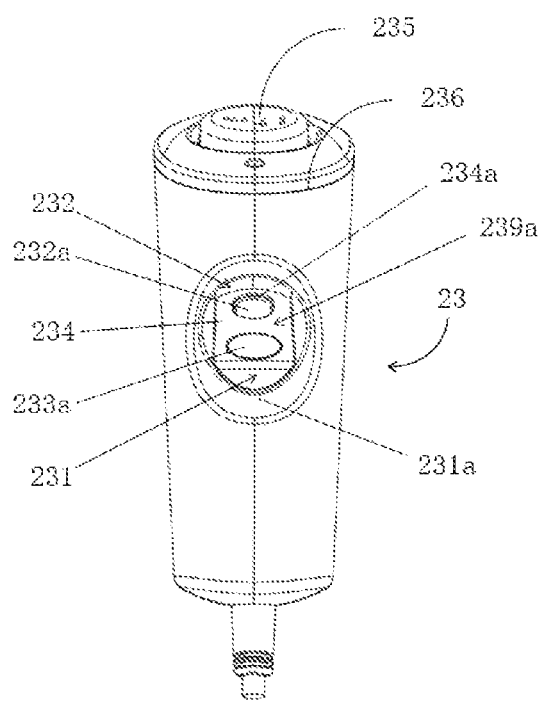
Figure 1C:
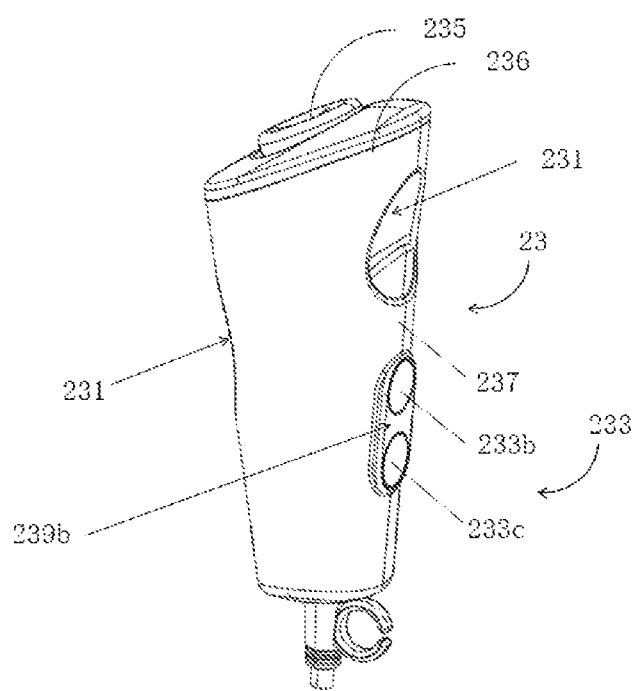

Please refer to FIG. 1A to FIG. 1C, FIG. 1A is a schematic diagram of a nursing call system 1 according to an embodiment of the present invention. FIG. 1B to FIG. 1C are schematic diagrams showing different perspectives of the holding device 23 of the nursing call system 1 of FIG. 1A. The nursing call system 1 of an embodiment of the present invention includes an emergency call device 10, a display screen 13 and an extension accessory 20. The extension accessory 20 is pluggably coupled to the emergency call device 10. The emergency call device 10 is disposed adjacent to a bed (not shown) from the outside to transmit an emergency call signal to a nursing station. In this embodiment, the emergency call device 10 can be disposed on the rear wall of the bed (not shown). In other embodiments, the emergency call device 10 can be disposed on one side of the bed (not shown), but not limited thereto. In other embodiments, the emergency call device 10 can be disposed on a movable device (such as a movable device having four wheels) to facilitate movement to a suitable location for increasing the convenience of use. In addition, in the embodiment, the display screen 13 can be a touch panel and disposed on the emergency call device 10. In other embodiments, the display screen 13 can be disposed on the holding device 23 or other portions of the nursing call system, but not limited thereto.

The emergency call device 10 includes a plurality of control buttons 11 and a connection member 12. The control buttons 11 can be used to trigger an emergency call signal, adjust the volume, etc.

The extension accessory 20 includes a connecting wire 21, a connecting end 22 and a holding device 23. The connecting end 22 is disposed at one end of the connecting wire 21 and used to connect the connection member 12 of the emergency call device 10 to enable electrical connection between the extension accessory 20 and the emergency call device 10. In this embodiment, the connecting member 12 is a jack, and the connecting end 22 is a connecting terminal, but is not limited thereto.

The holding device 23 is disposed at the other end of the connecting wire 21. The holding device 23 includes a hole 231, a physiological sensor assembly, a carrier 234, and an emergency call button 235. The physiological sensor assembly includes a first physiological sensor 232 and a second physiological sensor 233. The first physiological sensor 232 includes a sensing component 232a, and the second physiological sensor 233 includes a first sensing component 233a and a second sensing component 233b and a third sensing component 233c. In this embodiment, the hole 231 is a through hole penetrating through the holding device 23. In other embodiments, the hole may be a buried hole, that is, a recess that does not penetrate through the holding device 23, or a non-penetrating structure that a baffle is installed on an open of the hole, for blocking light from entering the hole, but is not limited thereto. The emergency call button 235 is disposed at the upper end 236 of the holding device 23 to trigger an emergency call signal.

The physiological sensor assembly is disposed to measure at least one physiological information, and the at least one physiological information is displayed on the display screen 13. The at least one sensing component of the physiological sensor assembly is disposed in the hole 231 to be contacted by a finger (not shown) of a first-hand (not shown) of a patient (not shown) on a bed to get the at least one physiological information. In this embodiment, the at least one sensing component includes the sensing component 232a of the first physiological sensor 232 and the first sensing component 233a of the second physiological sensor 233, and the physiological sensor assembly further includes the second sensing component 233b and the third sensing component 233c of the second physiological sensor 233. The sensing component 232a of the first physiological sensor 232 and the first sensing component 233a are disposed in the hole 231, and the second sensing component 233b and the third sensing component 233c are disposed on the outer surface 237 of the holding device 23. In other embodiments, the physiological sensor assembly may be a combination of the first physiological sensor 232, the second physiological sensor 233, and other physiological sensors, but is not limited thereto. In another embodiment, in order to meet the ergonomics and safety, the hole 231 is inclined toward the upper end 236 of the holding device 23, and an angle between the hole 23 and a center line of the holding device 23 in the up and down direction is between 105 degrees and 170 degrees, so that the finger can be easily pulled out from the hole 231 without being injured.

In addition, the sensing component 232a of the first physiological sensor 232 and the first sensing component 233a of the second physiological sensor 233 are disposed close and located at a first region 239a of the holding device 23, such as a region in the hole 231. The second sensing component 233b and the third sensing component 233c of the second physiological sensor 233 are both disposed on a second region 239b of the holding device 23, such as a portion of the outer surface of holding device 23. Further, the first region 239a and the second region 239b are separated from each other.

In the embodiment, a surface of the carrier 234 constitutes the first region 239a and is fixed in the hole 231, while the second region 239b is a portion of the outer surface 237 of the holding device 23. In other embodiments, the first region may be a portion of the outer surface of the holding device while the second region may be located in the hole, the first region and the second region may be both located in the hole, or the first region and the second region are both part of the outer surface of the holding device, but are not limited thereto.

The carrier 234 carries the sensing component 232a of the first physiological sensor 232 and the first sensing component 233a of the second physiological sensor 233. An alignment direction of the sensing component 232a of the first physiological sensor 232 and the first sensing component 233a is oriented toward an opening 231a of the hole 231. In other embodiments, the sensing component 232a of the first physiological sensor 232 and the first sensing component 233a of the second physiological sensor 233 are directly fixed, but are not limited thereto, in the hole.

Moreover, in the embodiment, the carrier 234 has a recess 234a to carry the sensing component 232a of the first physiological sensor 232. In other embodiments, the surface of the carrier 234 may be a flat surface, but is not limited thereto.

The first physiological sensor 232 is disposed to measure a first physiological information 26 which can be displayed on the display screen 13. The second physiological sensor 233 is disposed to measure a second physiological information 27 which can be displayed on the display screen 13. In this embodiment, the first physiological sensor 232 is a photo-plethysmographic sensor (PPG Sensor), and the first physiological information 26 is a photo-plethysmographic physiological information. The second physiological sensor 233 is an electrocardiographic sensor (ECG Sensor), and the second physiological information 27 is an electrocardiographic physiological information. The photo-plethysmographic physiological information includes, but is not limited to, blood oxygen concentration, heart rate, etc., and the electrocardiographic physiological information includes, but not limited to, ECG signals. In other embodiments, the first physiological sensor 232 and the second physiological sensor 233 may be other physiological sensors, not limited to a PPG sensor or an ECG sensor.

When a first-hand (not shown) of the patient (not shown) on the bed (not shown) holds the holding device 23, a finger of the first hand (not shown) penetrates into the hole 231 to contact the first sensing component 233a of the first physiological sensor 232 and the first sensing component 233a of the second physiological sensor 233, and a limb (not shown) of the patient (not shown) contacts the second sensing component 233b and/or the third sensing component 233c, the measured first physiological information 26 and the second physiological information 27 are displayed on the display screen 13. The limb contacting the second sensing component 233b and/or the third sensing component 233c is the other hand, the left foot or the right foot of the patient (not shown), so that the second physiological sensor 233 can measure the ECG signal. In this embodiment, the finger is an index finger (not shown), wherein the fingertip of the index finger (not shown) contacts the sensing component 232a of the first physiological sensor 232, and the other part of the index finger (not shown) contacts the first sensing component 233a. In other embodiments, any two parts of a finger can be used to respectively contact the sensing component 232a of the first physiological sensor 232 and the first sensing component 233a of the second physiological sensor 233, but are not limited thereto.

In addition, in the embodiment, the display screen 13 includes a measuring button 131 and an uploading button 132. The measuring button 131 is used to start the measurement of the first physiological information 26 and the second physiological information 27. The uploading button 132 is used to upload the first physiological information 26 and the second physiological information 27 to a medical information system for subsequent medical use. In other embodiments, the measuring button 131 or the uploading button 132 can be a control button, which can be set to the emergency call device 10 or the holding device 23, but is not limited thereto.

In the embodiment, the first physiological sensor 232 is a PPG sensor. For PPG sensors, the external light will affect the sensing results during the measurement. In view of the above, the invention provides a physiological sensor (such as the sensing component 232a of the first physiological sensor 232) disposed in the hole 231. Through the design of the hole 231, the external light that affects the physiological sensor is reduced, and the physiological sensing result is more accurate. Moreover, the design of the recess 234a of the carrier 234 can also reduce the influence of the external light on the physiological sensor, and the physiological sensing result can be more accurate.

The invention enables the physiological information to be transmitted directly and in real time to the medical information system through the nursing call system by integrating the physiological sensor assembly into the nursing call system. In this way, the workload of manual input by a caregiver can be reduced, the possible errors due to manual input can be avoided, and the real-time updating of the medical information system is helpful for real-time medical use.

Figure 2:
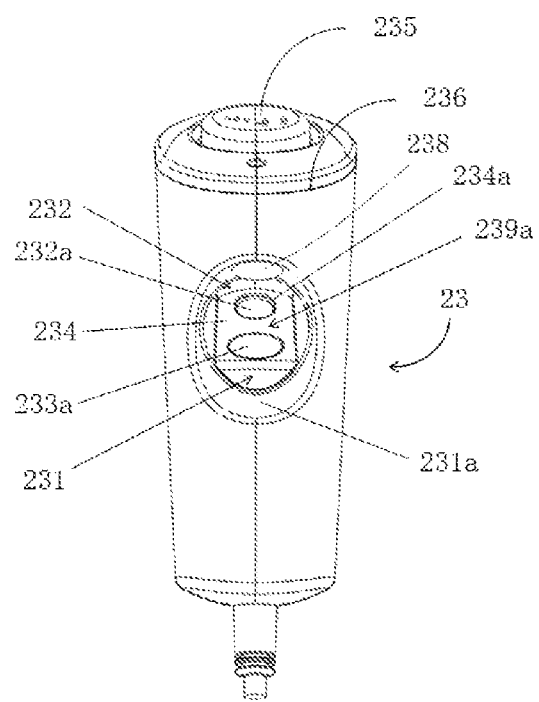
FIG. 2 is a schematic diagram of a holding device of a nursing call system according to another embodiment of the present invention.

Please refer to FIG. 2. FIG. 2 is a schematic diagram of the holding device 23 of the nursing call system 1 according to another embodiment of the invention. The nursing call system 1 of the embodiment is the same as or similar to the embodiment described in FIG. 1A to FIG. 1C, and the same or similar points are not described again. Only the main differences will be described below.

In the embodiment, the holding device 23 further includes a hollow elastic member 238 disposed in the hole 231 opposite to the carrier 234. The hollow elastic member 238 is disposed adjacent to the first physiological sensor 232, and an expansion direction of the hollow elastic member 238 is toward the sensing component 232a of the first physiological sensor 232. In an embodiment, the hollow elastic member 238 can be inflated. When the measuring button 131 is pressed, the hollow elastic member 238 is inflated and expanded toward the sensing component 232a of the first physiological sensor 232 to slightly press the finger in order to make the finger closer to the sensing component 232a of the first physiological sensor 232. This feature makes the first physiological information to be more accurate. In the embodiment, the hollow elastic member 238 is inflated by an inflation module (not shown) provided inside the holding device 23. In other embodiments, the inflation module may be disposed in the emergency call device 10, and the hollow elastic member 238 is inflated through a connecting line having an inflating passage, but is not limited thereto.

Figure 3:
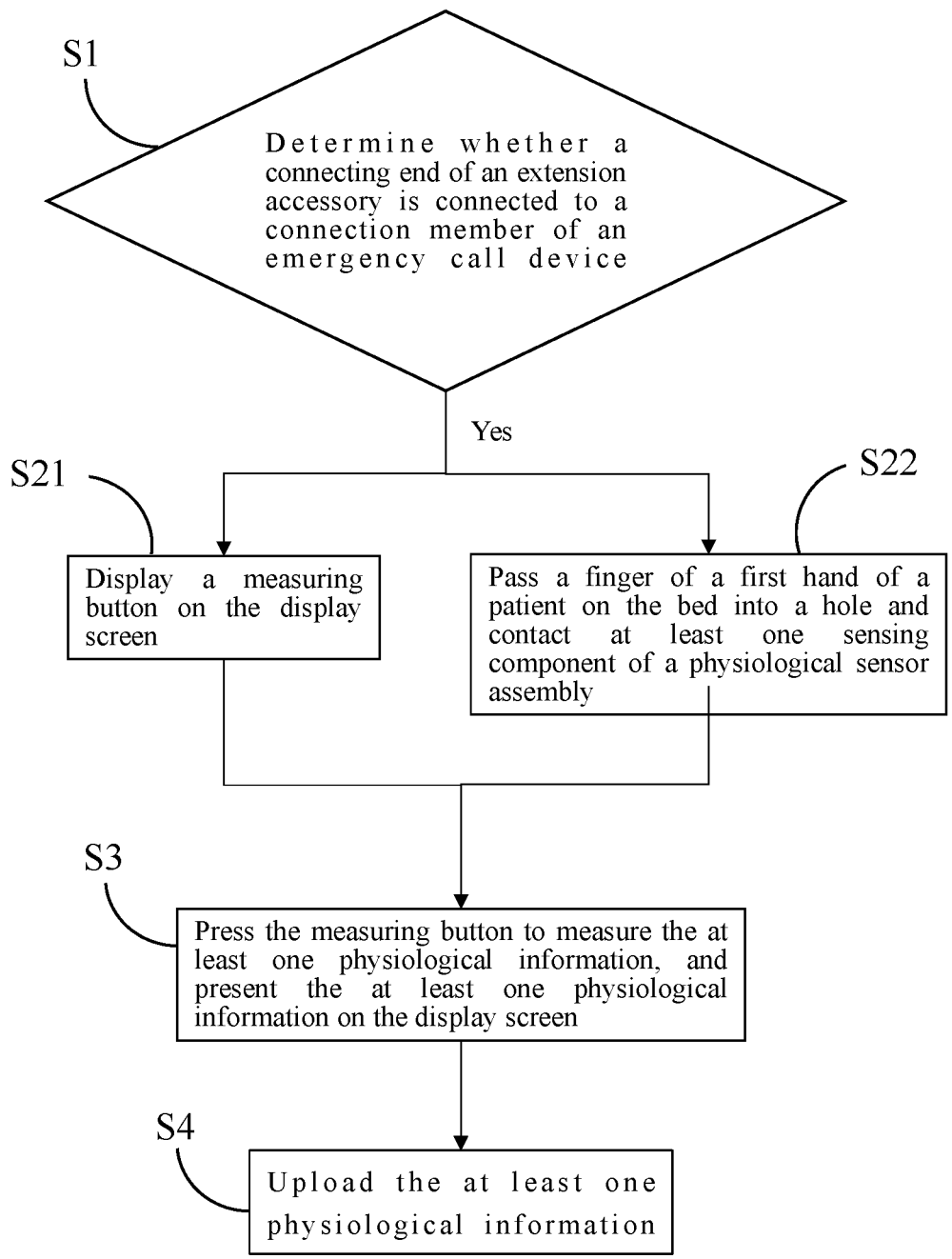
FIG. 3 is a schematic flow chart of a measuring method of a nursing call system according to an embodiment of the present invention.

Please refer to FIG. 3. FIG. 3 is a schematic flow chart of a measuring method of a nursing call system according to an embodiment of the present invention. The nursing call system 1 of the embodiment is the same as or similar to the implementation means and the contents described in FIG. 1A to FIG. 2, and the same or similar points are not be described again. The following mainly describes the measuring method of the nursing call system of the embodiment. The measuring method includes the following steps:

Step S1: To determine whether a connecting end 22 of an extension accessory 20 is connected to a connection member 12 of an emergency call device 10. If it is determined to be connected, continue the next step. If it is determined not to be connected, continue this determination until the connection is completed.

The nursing call system 1 includes the emergency call device 10, the extension accessory 20 and a display screen 13. The emergency call device 10 is disposed adjacent to a bed to transmit an emergency call signal to a nursing station. The emergency call device 10 includes the connecting member 12. The extension accessory 20 includes a connecting wire 21, the connecting end 22 and a holding device 23. the connecting end 22 is disposed at one end of the connecting wire 21 and disposed to connect the connecting member 12 of the emergency call device 10 to enable electrical connection between the extension accessory 20 and the emergency call device 10. The holding device 23 is disposed at the other end of the connecting wire 21.

Step S21: To display a measuring button 131 on the display screen 13. In the embodiment, the measuring button 131 may be a virtual button.

Step S22: To pass a finger of a first hand of a patient on the bed into a hole 231 and contact at least one sensing component of a physiological sensor assembly.

The holding device 23 includes the hole 231 and the physiological sensor assembly disposed to measure at least one physiological information. The at least one sensing component of the physiological sensor assembly is disposed in the hole 231.

Step S3: To press the measuring button 131 to measure the at least one physiological information, and to present the at least one physiological information on the display screen 13.

Step S4: To upload the at least one physiological information by pressing an uploading button 132. In the embodiment, the uploading button 132 can be displayed on the display screen 13 and may be a virtual button. In other embodiments, the uploading button 132 can be a control button set on the emergency call device 10 or on the holding device 23, but not limited thereto. Moreover, the at least one physiological information is transmitted to the medical information system in real time for subsequent medical use.

Figure 4:
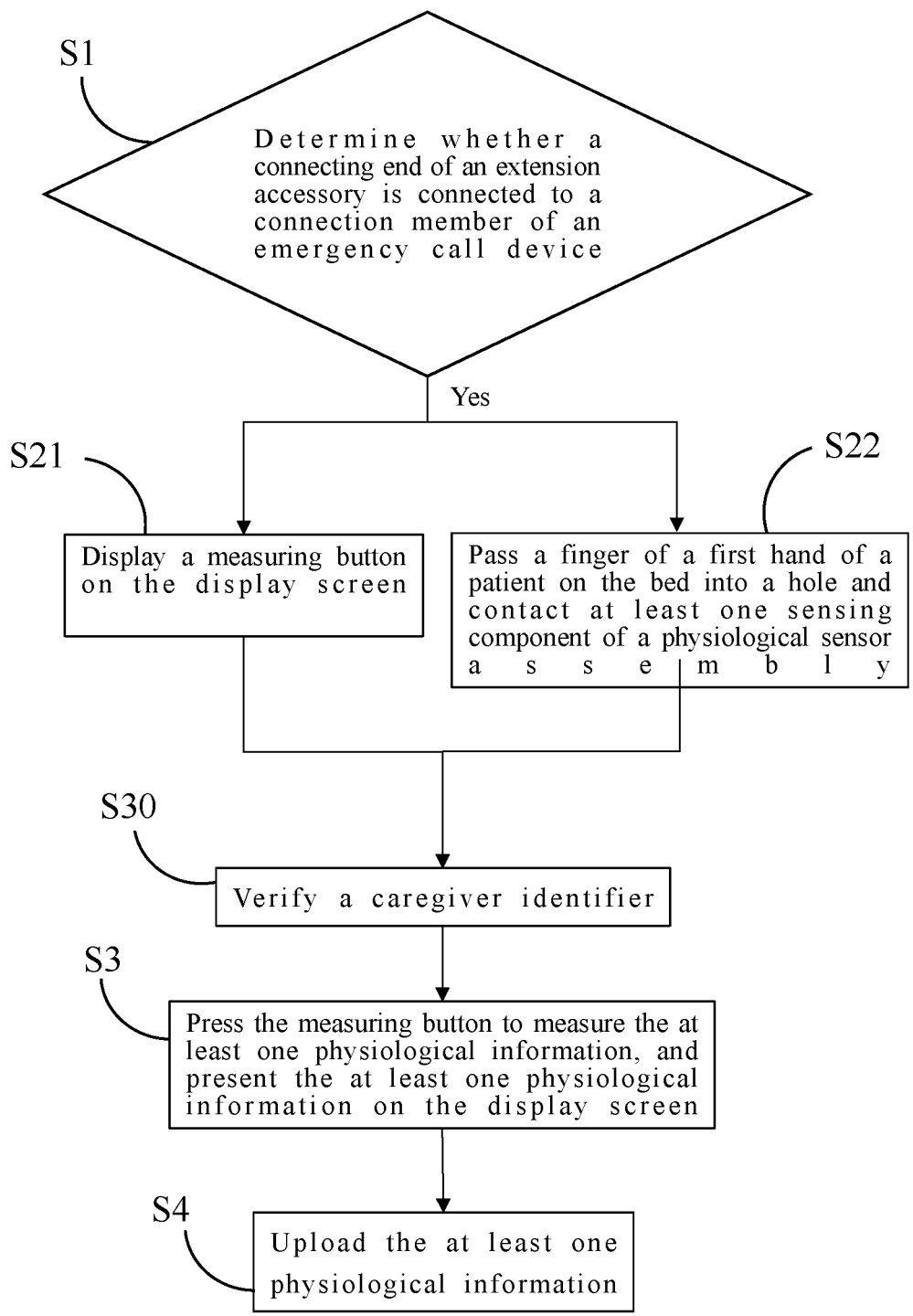
FIG. 4 is a schematic flow chart of a measuring method of a nursing call system according to another embodiment of the present invention.

Please refer to FIG. 4. FIG. 4 is a schematic flow chart of a measuring method of a nursing call system according to another embodiment of the invention. The measuring method of the embodiment is the same as or similar to the measuring method described in FIG. 3, and the same or similar points are not be described again. Only the main differences of the measuring method of this embodiment are described below.

The measuring method of this embodiment further includes:

Step S30: To verify a caregiver identifier. Only when the caregiver identifier is verified by the nursing call system 1 as a caregiver, the at least one physiological information can be measured, and the process proceeds to step S3. If the verification is still not completed, the process is not proceeded to step S3 until the verification is completed.

In the embodiment, a sensor of the nursing call system is sensed by a sensing card of a caregiver to complete the verification. In other embodiments, the verification may be completed by password input, face recognition, etc., but not limited thereto. In operation, the measurement and verification can be performed by a caregiver to ensure the correctness of physiological information.

Figure 5:
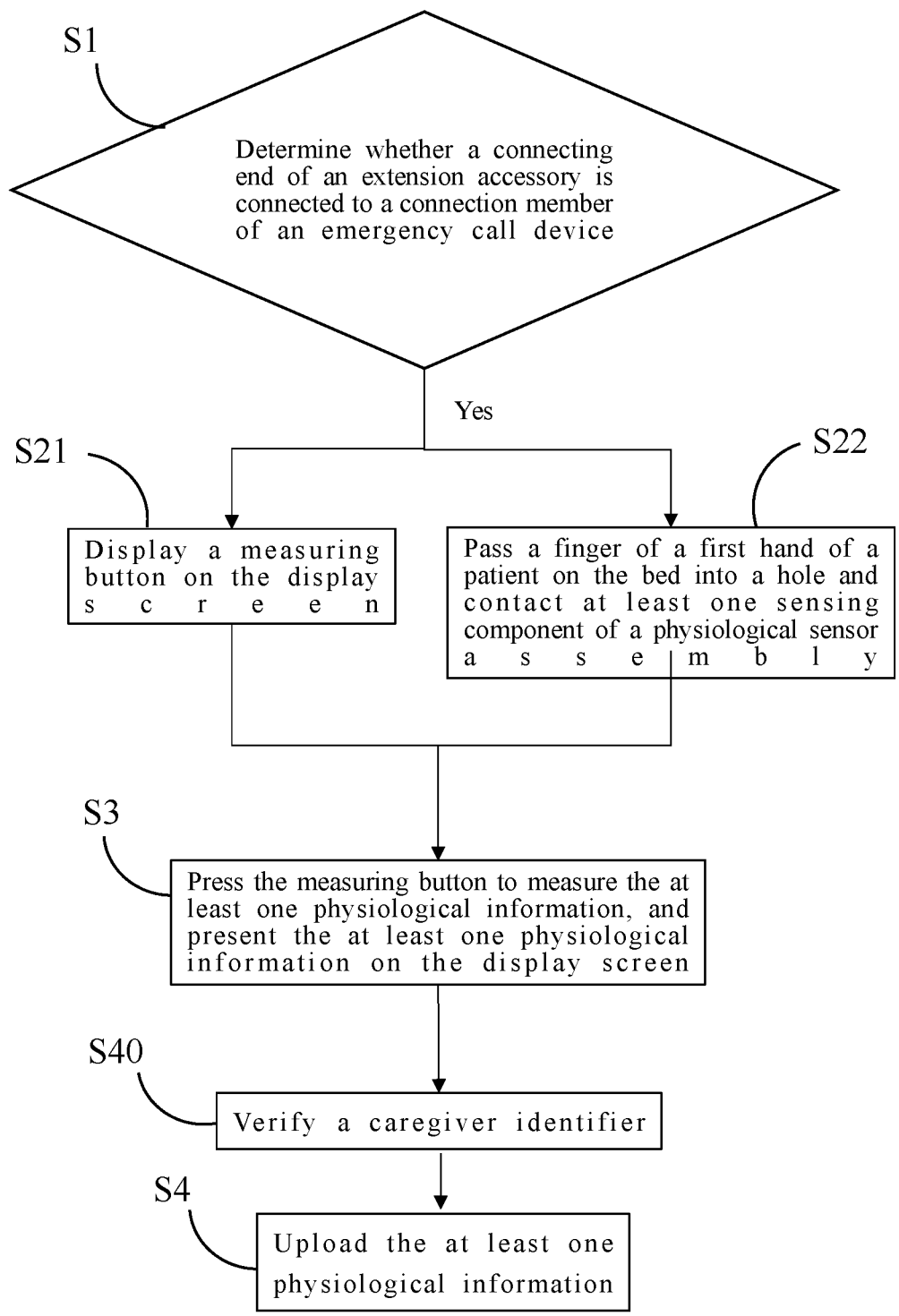
FIG. 5 is a schematic flow chart of a measuring method of a nursing call system according to still another embodiment of the present invention.

Please refer to FIG. 5. FIG. 5 is a schematic flow chart of a measuring method of a nursing call system according to still another embodiment of the present invention. The measuring method of the embodiment is the same as or similar to the measuring method described in FIG. 3, and the same or similar points are not be described again. Only the main differences of the measuring method of this embodiment are described below.

The measuring method of this embodiment further includes:

Step S40: verify a caregiver identifier. Only when the caregiver identifier is verified by the nursing call system 1 as a caregiver, the at least one physiological information can be uploaded, and the process proceeds to step S4. If the verification is still not completed, the process is not proceeded to step S4 until the verification is completed. In the embodiment, a sensor of the nursing call system is sensed by a sensing card of a caregiver to complete the verification. In other embodiments, the verification may be completed by password input, face recognition, etc., but not limited thereto. In operation, the measurement and verification can be performed by a caregiver to ensure the correctness of physiological information Having described at least one of the embodiments of the claimed invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents. Specifically, one or more limitations recited throughout the specification can be combined in any level of details to the extent they are described to accomplish the disclosed system and method.

What is claimed is:

1. A nursing call system, comprising:
an emergency call device comprising a connection member and being disposed adjacent to a bed to transmit an emergency call signal to a nursing station to make a nursing call;
a display screen; and
an extension accessory, comprising:
  a connecting wire;
  a connecting end disposed at one end of the connecting wire to connect the connection member of the emergency call device to enable electrical connection between the extension accessory and the emergency call device; and
  a holding device being disposed at the other end of the connecting wire and comprising:
    an emergency call button disposed on the holding device to trigger the emergency call signal;
    a first physiological sensor including a sensing component and being disposed to measure a first physiological information; and
    a second physiological sensor including a first sensing component and a second sensing component and being disposed to measure a second physiological information, the first sensing component and the sensing component of the first physiological sensor being disposed adjacent to each other and disposed at a first region of the holding device, the second sensing component being disposed at a second region of the holding device, the first region being separated from the second region;
wherein the measured first physiological information and the measured second physiological information are displayed on the display screen when a finger of a first hand of a patient on the bed contacts the sensing component of the first physiological sensor and the first sensing component, and a limb of the patient contacts the second sensing component.

2. The nursing call system according to claim 1, wherein the first physiological sensor is a photo-plethysmographic sensor, and the second physiological sensor is an electrocardiographic sensor.

3. The nursing call system according to claim 1, wherein the holding device further comprises a carrier and a hole, and the carrier forms the first region and is fixed in the hole, an alignment direction of the sensing component of the first physiological sensor and the first sensing component of the second physiological sensor located on the carrier is oriented toward an opening of the hole, the second region is a portion of an outer surface of the holding device, and the carrier has a recess carrying the sensing component of the first physiological sensor.

4. The nursing call system according to claim 1, wherein the holding device further comprises a hollow elastic member disposed in the hole, and an expanding direction of the hollow elastic member is toward the sensing component of the first physiological sensor.

5. The nursing call system according to claim 1, wherein the emergency call button is disposed at an upper end of the holding device.

6. A nursing call system, comprising:
an emergency call device comprising a connection member and being disposed adjacent to a bed to transmit an emergency call signal to a nursing station to make a nursing call;
a display screen; and
an extension accessory, comprising:
  a connecting wire;
  a connecting end disposed at one end of the connecting wire to connect the connection member of the emergency call device to enable electrical connection between the extension accessory and the emergency call device; and
  a holding device being disposed at the other end of the connecting wire and comprising:
    an emergency call button disposed at an upper end of the holding device to trigger the emergency call signal;
    a hole; and
    a physiological sensor assembly disposed to measure at least one physiological information displayed on the display screen, wherein at least one sensing component of the physiological sensor assembly is disposed in the hole to be contacted by a finger of a first hand of a patient on the bed to obtain the at least one physiological information.

7. The nursing call system according to claim 6, wherein the at least one sensing component comprises a first sensing component, the physiological sensor assembly further comprises a second sensing component, the first sensing component is disposed in the hole, the second sensing component is disposed on an outer surface of the holding device, the hole is inclined toward the upper end of the holding device, and an angle between the hole and a center line of the holding device in the up and down direction is between 105 degrees and 170 degrees.

8. A measuring method of a nursing call system, comprising steps of:
determining whether a connecting end of an extension accessory is connected to a connection member of an emergency call device, wherein the nursing call system comprises the emergency call device, the extension accessory and a display screen, the emergency call device is disposed adjacent to a bed to transmit an emergency call signal to a nursing station to make a nursing call, the emergency call device comprises the connection member, the extension accessory comprises a connecting wire, the connecting end and a holding device, the connecting end is disposed at one end of the connecting wire to connect the connection member of the emergency call device to enable electrical connection between the extension accessory and the emergency call device, and the holding device is disposed at the other end of the connecting wire to trigger the emergency call signal;
displaying a measuring button on the display screen;
passing a finger of a first hand of a patient on the bed into a hole and contacting at least one sensing component of a physiological sensor assembly, wherein the holding device includes the hole and the physiological sensor assembly disposed to measure at least one physiological information, and the at least one sensing component of the physiological sensor assembly is disposed in the hole; and
pressing the measuring button to measure the at least one physiological information and presenting the at least one physiological information on the display screen.

9. The measuring method of the nursing call system according to claim 8, further comprising a step of verifying a caregiver identifier, wherein the at least one physiological information is measured when the caregiver identifier is verified by the nursing call system as a caregiver.

10. The measuring method of the nursing call system according to claim 8, further comprising a step of verifying a caregiver identifier and uploading the at least one physiological information, wherein the at least one physiological information is uploaded when the caregiver identifier is verified by the nursing call system as a caregiver.

\* \* \* \* \*